US005563289A

United States Patent [19]
Sounik et al.

[11] Patent Number: 5,563,289
[45] Date of Patent: Oct. 8, 1996

[54] PROCESS FOR PREPARING ACETOXYSTYRENE

[75] Inventors: James R. Sounik; Keith M. Russ, both of Corpus Christi, Tex.

[73] Assignee: Hoechst Celanese Corporation, Somerville, N.J.

[21] Appl. No.: 542,583

[22] Filed: Oct. 13, 1995

[51] Int. Cl.[6] .................................................. C07C 67/297
[52] U.S. Cl. ................................................ 560/130; 560/239
[58] Field of Search ...................................... 560/130, 239

[56] References Cited

U.S. PATENT DOCUMENTS 5,041,614  8/1991  Aslam et al. ............................ 560/130

Primary Examiner—Samuel Barts
Attorney, Agent, or Firm—James J. Mullen; Donald R. Cassady

[57] ABSTRACT

The present invention provides a unique and novel way of producing an acetoxystyrene. In this new process which comprises a single step, a mixture of (a) a carbinol, (b) an acetylating agent, and (c) an acid catalyst is dehydrated under suitable dehydration conditions of temperature and pressure to form said acetoxystyrene.

13 Claims, No Drawings

PROCESS FOR PREPARING ACETOXYSTYRENE

BACKGROUND OF THE INVENTION

1. Field of the Invention

The present invention relates to a method for the preparation of an acetoxystyrene (ASM), and more particularly, for the preparation of 4-acetoxystyrene from a carbinol such as 4-hydroxyphenylmethylcarbinol (HPMC).

2. Description of the Prior Art

Acetoxystyrene (ASM) is a well-known compound which is useful as an intermediate in the preparation of compounds useful in the production of adhesives, photoresists, etc. The preparation of acetoxystyrene is well-known in the art; however, a more efficient process for preparing acetoxystyrene is desired and needed. The instant invention provides a method whereby reduced process steps are obtained.

The following prior art references are disclosed in accordance with the terms of 37 CFR 1.56, 1.97 and 1.93.

U.S. Pat. No. 5,087,772 (issued Feb. 11, 1992) discloses the preparation of 4-hydroxystyrene (HSM) by reacting 4-acetoxystyrene (ASM) with a suitable alcohol in the presence of a catalytic amount of a suitable base.

European Patent Application 0-128-984 (publication number) filed Aug. 30, 1983, discloses a process for the production of para-vinyl phenol (HSM) by dehydrogenation of paraethyl phenol.

European Patent Application 0-108-624 (publication number) filed Nov. 4, 1983, discloses a process for the production of p-vinyl phenol polymer (polyhydroxystyrene polymer—PHS) by polymerizing p-vinylphenol (HSM) in the presence of water and iron.

U.S. Pat. No. 4,032,513 (issued Jun. 28, 1977) discloses a process of producing PHS by cationically polymerizing HSM in the presence of a nitrile, such as $CH_3CN$, using a cationic polymerization initiator in a homogeneous reaction system.

U.S. Pat. No. 5,041,614 discloses a method for the preparation of 4-acetoxystyrene (ASM) from 4-acetoxyphenylmethylcarbinol. (Note Formula I for the structural formula for ASM).

U.S. Pat. No. 5,084,533 discloses a process for the neat hydrogenation of 4-acetoxyacetophenone in the production of 4-acetoxystyrene (ASM).

U.S. Pat. No. 5,151,546 discloses a process for preparing 4-acetoxystyrene (ASM) by heating 4-acetoxyphenylmethylcarbinol with an acid catalyst.

U.S. Pat. No. 5,245,074 discloses a process for preparing 4-acetoxystyrene (ASM) through the 4-acetoxyacetophenone/4-acetoxyphenylmethylcarbinol route.

U.S. Pat. No. 5,247,124 discloses a process for preparing substituted styrenes such as ASM by reacting a bisarylalkyl ether in the presence of an acid catalyst.

All of the above cited prior art and any other references mentioned herein are incorporated herein by reference in their entirety.

SUMMARY OF THE INVENTION

The present invention provides a unique and novel way of producing an acetoxystyrene (monomer) (ASM). In this new process, a mixture of a carbinol such as HPMC, an acid catalyst, and an acetylating agent is dehydrated under suitable conditions of temperature and pressure to form said acetoxystyrene.

In this manner, at least one processing step is eliminated, thus reducing the manufacturing costs.

DETAILED DESCRIPTION OF THE INVENTION

It has unexpectedly been found that ASM can be prepared directly from a carbinol. Thus, there is provided a unique process for preparing an acetoxystyrene which comprises the steps of dehydrating a mixture of a carbinol, an acetylating agent, and an acid catalyst under suitable dehydration conditions of temperature and pressure to form said acetoxystyrene.

The starting material used in the present invention process is a carbinol which has the general formula:

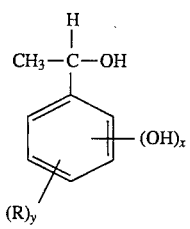

wherein R is selected from the group consisting of H, $C_{1-8}$ alkyl, and halogen (Cl, Br, F, and I); x is an integer of 1–5; and y is an integer of 0–4; with the proviso that x and y is always equal to 5.

One carbinol which has found uniqueness in the conversion to ASM is 4-hydroxyphenylmethylcarbinol (HPMC).

In this single step, process of the present invention, it is carried out at a reaction temperature of at least 100° C., preferably between 100° C. and 300° C., and more preferably between 100° C. and 250° C. The reaction pressure may be subatmospheric, atmospheric or superatmospheric. However, a pressure of about 1 torr. to about 100 torr. is generally preferred.

The length of time which this dehydration step is conducted is not critical and the only requirement is that the dehydration be conducted for a period sufficient to form ASM. Generally, this period is at least five seconds and may be as long as 25 hours.

The acetylation agent is acetic anhydride, acetyl chloride, or mixtures thereof. The amount of such agent used is not critical; however, it is necessary that the molar ratio of acetylation agent to carbinol to be at least about 1:1, preferably from about 1:1 to about 5:1.

The acetylation agent is used with a catalyst to facilitate the reaction. Any catalyst can be used as long as the desired end result is achieved. Preferably, acid catalysts are used. These acid catalysts include, without limitation, phosphoric acid, p-toluene-sulfonic acid, methane-sulfonic acid, ammonium bisulfate, potassium bisulfate, $H_2SO_4$ and HCl. The amount of catalyst required varies from catalyst to catalyst. In all instances, however, the amount is very small compared to the amount of reactant. In the present case, the amount of catalyst employed is usually less than one mole of catalyst per 100 moles of reactant, e.g. carbinol.

Diluents/Solvents which can be used in the present invention include: (a) hydrocarbons such as benzene, toluene, xylene, and low-boiling point petroleum fractions; (b) inorganic gases such as carbon monoxide, carbon dioxide, nitrogen, helium, and argon; (c) dipolar aprotic solvents; and (d) mixtures thereof. The dipolar aprotic solvents employed are solvents which have a high dielectric constant and a high dipole moment but no acid hydrogen atoms; for example, such solvents include dimethylsulfoxide (DMSO), acetonitrile, dimethylformamide (DMF), dimethylacetamide, hexamethylphosphoric acid triamide (HMPT), and n-methylpyrrolidone (NMP). Benzene and toluene are preferred diluents. The diluents are used in an amount of 2 to 200 moles, preferably 3 to 20 moles per mole of carbinol. It is to be understood that any diluent may be used under any temperature and reaction conditions so long as the acetylation of carbinol is effected smoothly.

The following specific examples are supplied for the purpose of better illustrating the invention. These examples are not intended, however, to limit or restrict the scope of the invention in any way and should not be construed as providing conditions, parameters, or values which must be utilized exclusively in order to practice the present invention.

Plug Flow Reactor Dehydration of
4-Hydroxyphenylmethylcarbinol (4-HPMC) in
Acetic Anhydride Example 1

A jacketed plug flow reactor was fitted with a peristaltic pump and feed reservoir, and the outlet was fitted with a 300 mL three neck flask fitted with a short path condenser and overhead receiver. The reactor was heated to 170° C. and then 107.3 g of a solution of 4-HPMC (10.69 g, 0.078 mole) in acetic anhydride (96.45 g) and phosphoric acid (0.15 g) was fed to the reactor at a rate of 8.3 g/min. The feed was stopped and there remained 29.06 g in the flask and 62.41 g in the overhead receiver. The material in the flask contained 25.7% 4-acetoxystyrene (7.47 g) and the overhead contained 2.0% 4-acetoxystyrene (1.24 g) which is a combined yield of 8.71 g (0.053 mole, 68.5%).

Example 2

A jacketed plug flow reactor was fitted with a peristaltic pump and feed reservoir, and the outlet was fired with a 250 mL three neck flask fitted with a short path condenser and overhead receiver. The reactor was heated to 150° C. and then 191.56 g of a solution of 4-HPMC (19.65 g, 0.142 mole) in acetic anhydride (171.60 g) and phosphoric acid (0.31 g) was fed to the reactor at a rate of 4.0 g/min. The feed was stopped and there remained 139.06 g in the flask and 50.26 g in the overhead receiver. The material in the flask contained 7.18% 4-acetoxystyrene (9.98 g) and the overhead contained 0.99% 4-acetoxystyrene (0.50 g) which is a combined yield of 10.48 g (0.064 mole, 44.9%).

Although the invention has been illustrated by the preceding examples, it is not to be construed as being limited thereby; but rather, the invention encompasses the genetic area as hereinbefore disclosed. Various modifications and embodiments can be made without departing from the spirit and scope thereof.

What is claimed is:

1. A process for preparing 4-acetoxystyrene which comprises the step of dehydrating a mixture of 4-hydroxyphenylmethylcarbinol, acetic anhydride, and an acid catalyst under suitable dehydration conditions of temperature and pressure to form 4-acetoxystyrene.

2. The process as set forth in claim 1 wherein the temperature is at least about 100° C.

3. The process as set forth in claim 1 wherein there is also present an acetylation catalyst.

4. The process as set forth in claim 1 wherein the reaction takes place in the presence of an organic solvent.

5. The process as set forth in claim 1 wherein the reaction takes place at a pressure of from about 1 torr. to about 100 torr.

6. The process as set forth in claim 1 wherein the temperature is from about 100° C. to about 300° C.

7. A process for preparing an acetoxystyrene which comprises the step of dehydrating a mixture of (a) a carbinol having the formula:

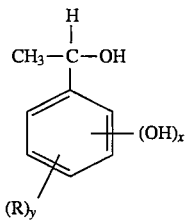

wherein R is selected from the group consisting of H, $C_1$–$C_8$ alkyl, and halogen; x is an integer of 1–5; and y is an integer of 0–4, with the proviso that x and y is always equal to 5; (b) an acetylating agent, and (c) an acid catalyst under suitable dehydration conditions of temperature and pressure to form said acetoxystyrene.

8. The process as set forth in claim 7 wherein the temperature is at least about 100° C.

9. The process as set forth in claim 7 wherein the reaction takes place in the presence of an aprotic organic solvent.

10. The process as set forth in claim 15 wherein the acetylation agent is selected from the group consisting of an acetic anhydride and acetyl chloride.

11. The process as set forth in claim 15 wherein the acetylation agent is acetic anhydride.

12. The process as set forth in claim 15 wherein the temperature is from about 100° C. to about 300° C.

13. A process for preparing an acetoxystyrene which comprises the steps of (a) mixing a carbinol with an acetylating agent in the presence of an acid catalyst to form a reaction mixture; and (b) dehydrating said reaction mixture under suitable dehydration conditions of temperature and pressure to form said acetoxystyrene; with the proviso that said carbinol has the formula:

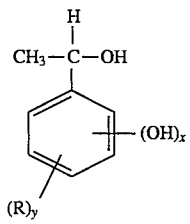

wherein R is selected from the group consisting of H, $C_1$–$C_8$ alkyl, and halogen; x is an integer of 1–5; and y is an integer of 0–4, with the proviso that x and y is always equal to 5.

* * * * *